US00PP13396P3

(12) United States Plant Patent
Evers

(10) Patent No.: US PP13,396 P3
(45) Date of Patent: Dec. 24, 2002

(54) ROSE PLANT NAMED 'TANABAMAR'

(75) Inventor: Hans-Jürgen Evers, Uetersen (DE)

(73) Assignee: Rosen Tantau Mathias Tantau Nachfolger (DE)

( * ) Notice: Subject to any disclaimer, the term of this patent is extended or adjusted under 35 U.S.C. 154(b) by 0 days.

(21) Appl. No.: 09/742,926

(22) Filed: Dec. 20, 2000

(65) Prior Publication Data

US 2002/0078479 P1 Jun. 20, 2002

(51) Int. Cl.[7] ..... A01H 5/00
(52) U.S. Cl. ..... Plt./108
(58) Field of Search ..... Plt./108, 150, 102, Plt./141

(56) References Cited

PUBLICATIONS

UPOV–ROM GTITM Computer Database 2001/06, GTI Jouve Retrieval Software, Citation for Rosa 'Tanabamar'.*

* cited by examiner

*Primary Examiner*—Bruce R. Campell
*Assistant Examiner*—June Hwu
(74) *Attorney, Agent, or Firm*—Webb Ziesenheim Logsdon Orkin & Hanson, P.C.

(57) ABSTRACT

The new cultivar is a variety of a shrub-like rose plant having a flat bushy growth habit. The long stem flowers are large, have an interesting coloration, and a pleasant fragrance. The plant exhibits good hardiness and resistance to most diseases.

1 Drawing Sheet

CLASSIFICATION

*Rosa l.*

VARIETAL DENOMINATION

'Tanabamar'.

BACKGROUND OF THE NEW PLANT

The present invention includes a new and distinct cultivar of *Rosa l.* known by the varietal name 'Tanabamar'.

The new plant was discovered in 1992 by the breeder in Ueterson, Germany in a controlled breeding program. The female parent (Breeder Ref. No. RT 8349) is an unpatented bi-colored yellow floribunda F1 numbered variety from the breeder's private collection which is maintained proprietary by the assignee. The male parent (Breeder Ref. No. RT 8342) is unpatented and also a numbered variety from this collection and is a red groundcover. The plant was discovered by the breeder on the Tanotax plantation in Ueterson, Germany. The plant can be propagated asexually on *Rosa canina* rootstock by cuttings and has been so asexually reproduced in Uetersen, Germany.

The variety is distinguishable by its large flowers, its fragrance and coloration, its shrub like appearance, and its resistance to diseases. Continued observations from the vegetative cuttings in Uetersen, Germany have confirmed that the distinguishing features of this new cultivar come true, remain stable, and are retained through successive propagations.

DESCRIPTION OF THE DRAWING

The accompanying photographic drawing illustrates the new cultivar. Colors are described in reference to The 1966 R.H.S. Colour Chart of The Royal Horticultural Society of London.

DESCRIPTION OF THE NEW PLANT

The following description sets forth the characteristics of the new cultivar.

THE PLANT

Size:
- *Height.*—60 cm.
- *Width.*—80 cm.

Habit: Flat bushy, long stems.
Growth vigor: Very strong.
Wood color:
- *New.*—Greyed-Green Group 191A.
- *Old.*—Greyed-Green Group 197A.

Thorns:
- *Color.*—Immature: Yellow-Green Group 147B. Mature: Greyed-Red Group 181A.
- *Size.*—0.9 cm (mature).
- *Shape.*—Hooked downward.
- *Location on stems and branches.*—Generally random locations with nearly no thorns at the top of stem.

Disease resistance: Robust to downy mildew and black spot.
Winter hardiness: Very good.

FOLIAGE

Arrangement: Imparipinnate.
Number of leaflets on typical stem leaves: 3–5.
Leaflets:
- *Size.*—6 cm long; 2.5 cm wide.
- *Color.*—Green Group 131A. Upper surface: Green Group 131A. Lower surface: Green Group 131D.
- *Shape.*—Oval overall with elongated apex and cordate base.
- *Texture.*—Leathery.
- *Margin.*—Serrated.

Petiole rachis:
- *Color.*—Green Group 139A.
- *Texture.*—Smooth.

*Stipules.*—Size: 4 cm long; 1.6 cm wide. Shape: Bearded.

BUD

Size: 1.8 cm long; 1.2 cm wide.
Shape: Rounded.
Color: Red Group 46A at edges with remainder Orange Group 26B.
Color changes during opening: None.
Sepals:
*Size.*—2.6 cm long; 0.8 cm wide.
*Color.*—Green Group 139B.
*Texture.*—Some hairs on upper side colored Green Group 128D.
*Quantity of foliaceous appendages.*—2.
Receptacle:
*Size.*—1.4 cm long.
*Color.*—Green Group 137A.
*Shape.*—Funnel.
*Texture.*—Smooth.
Peduncle:
*Color.*—Green Group 141B.
*Length.*—Approximately 1.5 cm.
*Strength.*—Stiff.
*Texture.*—Glandular.

FLOWER

Borne (number in clusters): 3–4.
Size (diameter): Approximately 7 cm.
Form: High-centered.
Petals:
*Number per flower.*—Approximately 20.
*Color.*—Upper surface: Red Group 46B with basal spot of Purple Group 75C. Lower surface: Red Group 43A which changes with maturity to Red Group 43B.
*Texture.*—Soft.
*Size.*—Medium; 3–4 cm.
*Shape.*—Elliptic with obtuse apex and cordate base.
*Margin.*—Entire.
*Persistence.*—Petals drop off cleanly before drying.
*Lastingness.*—Approximately 5 days on a cut flower.
Petaloids:
*Size.*—2 cm long; 0.8 cm wide.
*Color.*—Same as petals.
*Quantity.*—2–6 per flower.
Fragrance: Sweet, but usually none.
Blooming period: In mid-Europe, blooms from early July to late October.

REPRODUCTIVE ORGANS

Stamens:
*Number.*—36 per flower.
*Anther.*—Length: 0.1 cm. Color: Orange Group 25A.
*Filament.*—Length: 0.7 cm. Color: Orange Group 25A. Pollen color: Orange Group 26B.
Pistils:
*Number.*—Approximately 15.
*Style.*—Color: Orange-Red Group 34A. Length: 0.3 cm.
*Stigma.*—Color: Yellow-Orange Group 17A. Length: 0.5 cm.

No hips, fruit, or seed produced.

I claim:

1. A new and distinct variety of rose plant substantially as shown and described.

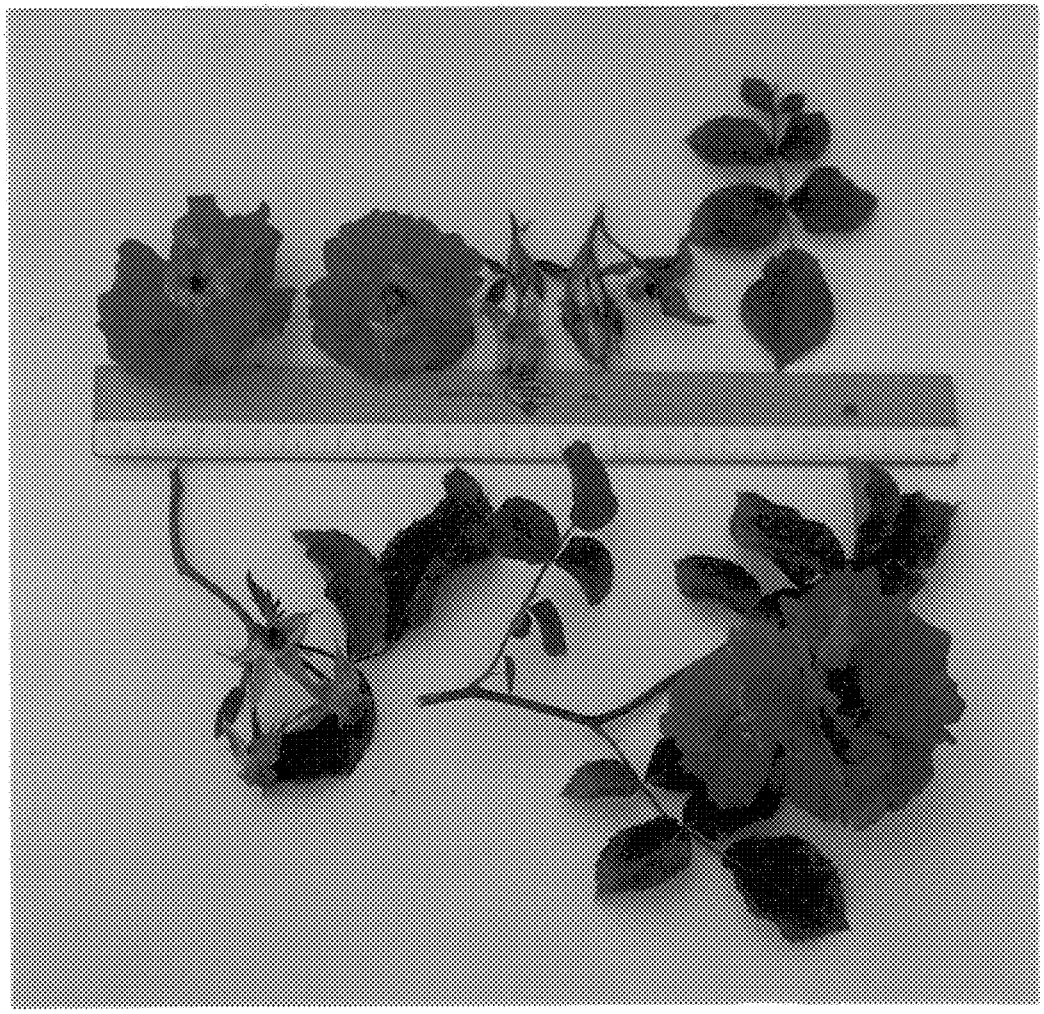

* * * * *